United States Patent

Sato et al.

[11] Patent Number: 5,840,976
[45] Date of Patent: Nov. 24, 1998

[54] METHOD OF STABILIZING N-VINYLAMIDES

[75] Inventors: Shin-Ichi Sato; Kiyoji Kuma; Toshimitu Inoue; Yuuichi Nishida, all of Kitakyushu, Japan

[73] Assignee: Mitsubishi Chemical Corporation, Tokyo, Japan

[21] Appl. No.: 724,036

[22] Filed: Sep. 23, 1996

Related U.S. Application Data

[63] Continuation of Ser. No. 447,156, May 22, 1995, abandoned.

[30] Foreign Application Priority Data

May 30, 1994 [JP] Japan ................................. 6-116533

[51] Int. Cl.$^6$ ...................... C07C 209/82; C07C 209/84; C07C 209/90
[52] U.S. Cl. .................. 564/4; 564/2; 564/204; 564/206
[58] Field of Search .................. 564/2, 4, 215, 564/216, 206, 204

[56] References Cited

U.S. PATENT DOCUMENTS

| | | | |
|---|---|---|---|
| 2,758,135 | 8/1956 | Miller | 564/4 |
| 2,787,634 | 4/1957 | Coover et al. | 564/4 |
| 3,022,292 | 2/1962 | Sims | 564/2 |
| 4,814,505 | 3/1989 | Kroener et al. | 564/216 |
| 5,186,257 | 2/1993 | Stahl | 166/273 |
| 5,326,909 | 7/1994 | Kroener et al. | 564/4 |

FOREIGN PATENT DOCUMENTS

| | | |
|---|---|---|
| 43 28 950 A1 | 3/1994 | Germany . |
| 62-039553 | 2/1982 | Japan ........... 564/2 |
| 57-109749 | 7/1982 | Japan ........... 564/4 |
| 61-289068-A | 12/1986 | Japan . |
| 62-195352-A | 8/1987 | Japan . |
| 63-264559-A | 11/1988 | Japan . |
| 2-270846-A | 11/1990 | Japan . |
| 6-122661-A | 5/1994 | Japan . |
| 06220373 | 8/1994 | Japan . |

*Primary Examiner*—Shailendra Kumar
*Attorney, Agent, or Firm*—David G. Conlin; Cara Z. Lowen

[57] ABSTRACT

Disclosed herein is a method of improving the stability of N-vinylamides. A quinone or alkali-modified quinone is added to the N-vinylamide. The loss of the N-vinylamide due to polymerization and/or decomposition during distillation is significantly reduced.

11 Claims, No Drawings

METHOD OF STABILIZING N-VINYLAMIDES

This application is a continuation of application Ser. No. 08/447,156 filed on May 22, 1995, now abandoned.

BACKGROUND OF THE INVENTION

The present invention relates to a method of stabilizing an N-vinylamide, more particularly a method for preventing the loss of an N-vinylamide during distillation thereof.

N-vinylamides are readily polymerizable compounds and may be homopolymerized or copolymerized together with other vinyl compound(s) to provide (co)polymers with various properties. When these (co)polymers are then hydrolyzed, the amido group is converted into a primary amino group.

The N-vinylamides include N-vinylformamide and N-vinylacetamide, both of which are prepared through thermal decomposition. One of typical processes for the preparation thereof is the thermal decomposition of corresponding N-($\alpha$-alkoxyethyl)-amides.

N-vinylamides are very reactive and may readily be decomposed or polymerized. In order to avoid such decomposition and polymerization in obtaining N-vinylamides by distillation from the thermal decomposition products of the corresponding N-($\alpha$-alkoxyethyl)amides, various methods have been proposed in, for example, JP-A-62-19352 and JP-A-63-246659. Further, attempts to stabilize the N-vinylamides during the storage or distillation by adding some stabilizers thereto have also been proposed in JP-A-61-289068, JP-A-2-270846, JP-A-6-122660 and DE-A-43 28 950.

However, these known methods for stabilizing N-vinylamides are not always satisfactory.

SUMMARY OF THE INVENTION

A primary object of the present invention is, therefore, to provide a method of stabilizing an N-vinylamide, more specifically a method for preventing the loss of an N-vinylamide, particularly N-vinylformamide, during the distillation thereof to obtain a purified N-vinylamide.

According to the present invention, the stability of an N-vinylamide can be significantly improved by adding a quinone or its alkali-modified derivative to the N-vinylamide.

DESCRIPTION OF THE INVENTION

The invention will be described in detail.

N-vinylamides to be stabilized according to the present invention may be either crude or purified materials. Thus, according to the present invention, in a process for preparing an N-vinylamide comprising distilling the N-vinylamide obtained from the thermal decomposition step to purify, a stabilizer may be added to the thermal decomposition product to stabilize the N-vinylamide during the distillation step. Alternatively, the stabilizer may be added to the purified N-vinylamide to enhance the stability thereof during storage and transport of the purified products.

The stabilizer added to the N-vinylamide in the present invention may be either a quinone or an alkali-modified derivative thereof. Quinones are diketone compounds derived from aromatic hydrocarbons, in which two CH groups in the aromatic ring have been converted into CO groups while double bonds have been transferred in the molecule as required to form a quinoid structure. The quinone compounds include benzoquinones such as p- and o-benzoquinone, naphthoquinones, and anthraquinones. The quinone compounds may have one or more substituents in their ring, including hydroxyl, alkyl with about 1 to 4 carbon atoms, and alkoxyalkyl groups with about 1 to 4 carbon atoms. Illustrative examples of the compounds may include methyl-p-benzoquinone, 4-o-toluquinone, o-, m- and p-xyloquinone, 4,5-xylo-o-quinone, methoxy-p-benzoquinone, and diphenoquinone. Preferably, the quinone is a benzoquinone, more preferably p-benzoquinone.

The alkali-modified derivatives of quinones used in the present invention may be produced in an alkaline solution of a quinone. Although their details have been unknown, it is believed that they are non-volatile and are some polymers of a quinone. The alkali-modified quinones may be readily produced in a few tens minutes to several hours when a solution of a quinone in a solvent such as methanol is allowed to stand at room temperature after adding thereto a very small amount (e.g., about $10^{-3}$ mol/l) of sodium or potassium hydroxide. The conversion of a quinone into its alkali-modified derivative can be easily confirmed by the absence of the quinone in the solution when analyzed by liquid chromatography. Further, no quinone or decomposition products thereof can be detected when the solution is analyzed by gas chromatography. On the basis of this fact, it may be confirmed that the quinones may have been polymerized to some high boiling point materials.

The alkali-modified quinone added to the N-vinylamide according to the present invention may either be preliminarily prepared or may be produced in situ in an alkaline N-vinylamide solution by adding a quinone to the N-vinylamide. When the alkali-modified quinone is produced within the N-vinylamide solution, this solution should be preferably have a pH of 8 or higher. Generally, the larger the pH, the faster the alkali-modified quinone is produced. The pH in this context is measured in a solution of one part by volume of an N-vinylamide in 5 parts by volume of water.

When the alkali-modified quinone is prepared preliminarily, a quinone may be dissolved in a solvent capable of being easily separated from the N-vinylamide by distillation, such as methanol, ethanol, water, toluene, benzene or formamide, at a concentration of 5 to 150 g/l and an alkali such as sodium hydroxide, potassium hydroxide, sodium carbonate or sodium bicarbonate may be added thereto followed by stirring at room temperature or while heating. The amount of alkali added may be about $10^{-4}$ to $10^{-2}$ mol/l.

The amount of a quinone added to the N-vinylamide is usually 50 to 10,000 ppm, preferably 100 to 5,000 ppm. Smaller amounts thereof would not provide satisfactory effects. On the contrary, if larger amounts of quinone are added, the stabilizing effect may be saturated or no longer improved and eventually some adverse effect may be caused on the N-vinylamide upon use. When an alkali-modified quinone is used, it is added in such an amount that the amount of the corresponding quinone from which the alkali-modified quinone is derived should fall within the above mentioned range.

Both a quinone and an alkali-modified quinone are effective to stabilize an N-vinylamide, although the alkali-modified quinone is generally preferred. A quinone may generally act as a polymerization inhibitor and, therefore, it is desirable to distill the N-vinylamide stabilized therewith to remove the quinone before use. However, having a relatively high vapor pressure, the quinone may possibly be distilled out together with the N-vinylamide. On the other hand, an alkali-modified quinone is non-volatile and therefore readily separated from the N-vinylamide by distillation. Accordingly, an alkali-modified quinone is preferably used in the present invention.

EXAMPLES

The present invention will be further illustrated by the following examples but is not limited thereto without departing from the scope of the invention defined in the appended claims. In the examples, meq represents milli equivalent ($10^{-3}$ equivalent). The decomposition (%) of an N-vinylamide and the amount (ppm) of polymer produced are calculated in the following manner.

Decomposition (%): The concentrations of an N-vinylamide before and after heating (referred to as "$C_{before}$" and "$C_{after}$", respectively) were measured by liquid chromatography. Decomposition (%) was calculated from the equation:

$$(C_{before} - C_{after})/C_{before} \times 100$$

Polymer Production (ppm): To 50 g of a solution after heating, 250 g of acetone was added, and the insoluble materials were filtered out with $0.5\mu$ teflon filter. This was dried under reduced pressure at 60° C. until the weight thereof became unchanged. Polymer production (ppm) was calculated from the equation:

(Dry weight of insoluble material/50)$\times 10^6$

Examples 1 to 3 and Comparative Examples 1 to 10

A major portion of methanol was removed by distillation under reduced pressure from a thermal decomposition product solution of N-(α-methoxyethyl)formamide. Various reagents shown in Table 1 were added to the resulting crude N-vinylformamide containing 92% N-vinylformamide, 4.2% formamide and 3.8% other organics, followed by heating at 110° C. under nitrogen at normal pressure for one hour. The results are shown in Table 1.

TABLE 1

|  | Additive | Amount (ppm) | Decomposition (%) | Polymer (ppm) |
|---|---|---|---|---|
| Comp. Ex. 1 | — | — | 9.1 | 25200 |
| Ex. 1 | p-Benzoquinone | 3000 | 3.4 | 50 |
| Ex. 2 | ditto | 500 | 4.6 | 100 |
| Ex. 3 | Anthraquinone | 3000 | 10.0 | 200 |
| Comp. Ex. 2 | Cupferron* | 3000 | 9.0 | 1300 |
| Comp. Ex. 3 | N,N-Diphenyl-p-phenylenediamine | 3000 | 9.2 | 1100 |
| Comp. Ex. 4 | Benzoic acid | 3000 | 8.9 | 4000 |
| Comp. Ex. 5 | Hydroquinone | 3000 | 26.0 | 500 |
| Comp. Ex. 6 | p-Phenylenediamine | 3000 | 33.1 | 400 |
| Comp. Ex. 7 | 4-t-Butylcatechol | 3000 | 40.0 | 100 |
| Comp. Ex. 8 | ditto | 100 | 15.1 | 400 |
| Comp. Ex. 9 | Catechol | 3000 | 37.3 | 200 |
| Comp. Ex. 10 | Hydroquinone monomethylether | 3000 | 21.0 | 3700 |

*Phenylnitrosohydroxylamine ammonium

Example 4 p-Benzoquinone was dissolved in methanol at a concentration of 5%. To this solution 20 meq/kg of sodium hydroxide was added followed by stirring at 20° C. for 3 hours. Upon analysis by liquid chromatography, no p-benzoquinone was detected (lower limit for detection: 50 ppm), indicating that all p-benzoquinone was converted into an alkali-modified quinone.

To the same crude N-vinylformamide as in Example 1, the alkali-modified p-benzoquinone obtained above was added so that the amount of p-benzoquinone added was 3,000 ppm. The crude N-vinylformamide was subjected to simple distillation under reduced pressure of 5 torr at a bath temperature of 110° C. to distill out 90% of N-vinylformamide. The distilled out N-vinylformamide was analyzed by liquid chromatography but no p-benzoquinone was detected.

On the other hand, when 3000 ppm of p-benzoquinone was added instead of the alkali-modified quinone followed by immediate distillation, the distilled out N-vinylformamide contained 1,550 ppm of p-benzoquinone.

Example 5

In the same crude N-vinylformamide as in Example 1, p-benzoquinone was dissolved at a concentration of 5%. To this solution 50 meq/kg of sodium hydroxide was added followed by stirring at 10° C. for 1 hour. Upon analysis by liquid chromatography, no p-benzoquinone was detected, indicating that all p-benzoquinone was converted into an alkali-modified quinone.

The treated solution was subjected to simple distillation under reduced pressure of 5 torr at a bath temperature of 110° C. to distill out 90% of N-vinylformamide. No p-benzoquinone was detected in the distilled out N-vinylformamide.

Example 6

The thermal stability test was conducted in the same manner as in Example 1 except that the alkali-modified p-benzoquinone obtained in Example 4 or 5 was added instead of p-benzoquinone to the same crude N-vinylformamide as in Example 1. No significant difference from the case of p-benzoquinone added was found in both decomposition and polymer production.

According to the present invention, the stability of an N-vinylamide can be significantly improved by adding a quinone or its alkali-modified derivative to the N-vinylamide.

What is claimed is:

1. A method of stabilizing N-vinylformamide comprising adding p-benzoquinone to the N-vinylformamide.

2. The method of claim 1, which comprises adding 50 to 10,000 ppm of p-benzoquinone to the N-vinylformamide.

3. A method of purifying an N-vinylamide comprising distilling the N-vinylamide in the presence of an alkali-modified derivative of a quinone.

4. The method of claim 3, which comprises adding an alkali-modified derivative of a quinone to the N-vinylamide followed by distilling.

5. The method of claim 3, which comprises adding a quinone to an alkaline N-vinylamide and converting the quinone into a non-volatile material followed by distilling.

6. The method of claim 3, wherein the amount of an alkali-modified derivative of a quinone present is 50 to 10,000 ppm as calculated as the quinone.

7. The method of claim 3, wherein the N-vinylamide is N-vinylformamide.

8. The method of claim 3, wherein the quinone is p-benzoquinone.

9. A method of stabilizing N-vinylformamide comprising adding an alkali-modified derivative of a quinone to the N-vinylformamide.

10. The method of claim 9, which comprises adding 50 to 10,000 ppm of an alkali-modified derivative of a quinone to the N-vinylformamide, the amount of alkali-modified derivative added being calculated as a quinone from which it is derived.

11. The method of claim 3, wherein the quinone is a benzoquinone.

* * * * *